(12) United States Patent
Hackett (10) Patent No.: US 6,866,655 B2
(45) Date of Patent: Mar. 15, 2005

(54) MEDICAL DEVICE WITH ATRAUMATIC TIP

(75) Inventor: Steven S. Hackett, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 15 days.

(21) Appl. No.: 10/128,403

(22) Filed: Apr. 23, 2002

(65) Prior Publication Data

US 2003/0199849 A1 Oct. 23, 2003

(51) Int. Cl.[7] ............................................. A61M 25/00
(52) U.S. Cl. ..................................... 604/264; 513/107
(58) Field of Search ........................... 604/272, 264, 604/507, 508, 509, 513, 104, 107; 607/120, 122

(56) References Cited

U.S. PATENT DOCUMENTS

| | | |
|---|---|---|
| 4,385,635 A | 5/1983 | Ruiz |
| 4,531,943 A | 7/1985 | Van Tassel et al. |
| 4,551,292 A | 11/1985 | Fletcher et al. |
| 4,588,398 A | 5/1986 | Daugherty et al. |
| 5,165,420 A | 11/1992 | Strickland |
| 5,234,416 A | 8/1993 | Macaulay et al. |
| 5,447,503 A | 9/1995 | Miller |
| 5,569,218 A | 10/1996 | Berg |
| 5,599,319 A | 2/1997 | Stevens |
| 5,603,705 A | 2/1997 | Berg |
| 5,628,761 A | 5/1997 | Rizik |
| 5,674,208 A | 10/1997 | Berg et al. |
| 5,680,873 A | 10/1997 | Berg et al. |
| 5,733,248 A | 3/1998 | Adams et al. |
| 5,769,819 A | 6/1998 | Schwab et al. |
| 5,827,225 A | 10/1998 | Ma Schwab |
| 5,851,464 A | 12/1998 | Davila et al. |
| 5,853,400 A | 12/1998 | Samson |
| 5,855,560 A | 1/1999 | Idaomi et al. |
| 5,860,963 A | 1/1999 | Azam et al. |
| 5,911,715 A | 6/1999 | Berg et al. |
| 5,957,893 A | 9/1999 | Luther et al. |
| 6,113,579 A * | 9/2000 | Eidenschink et al. ........ 604/264 |
| 6,210,370 B1 * | 4/2001 | Chi-sing et al. ............ 604/164 |
| 6,245,053 B1 | 6/2001 | Benjamin |
| 6,322,586 B1 | 11/2001 | Monroe et al. |
| 6,368,301 B1 | 4/2002 | Hamilton et al. |
| 2001/0016702 A1 | 8/2001 | Benjamin |
| 2002/0052641 A1 | 5/2002 | Monroe et al. |
| 2002/0082550 A1 | 6/2002 | Hamilton et al. |
| 2004/0030259 A1 * | 2/2004 | Dae et al. .................... 600/549 |
| 2004/0118415 A1 * | 6/2004 | Hall et al. ................... 128/898 |

FOREIGN PATENT DOCUMENTS

| | | |
|---|---|---|
| FR | 2220283 | 10/1974 |
| WO | WO 96/18431 | 6/1996 |
| WO | WO 99/44666 | 9/1999 |

* cited by examiner

*Primary Examiner*—Sharon Kennedy
(74) *Attorney, Agent, or Firm*—Crompton, Seager & Tufte, LLC (57) ABSTRACT

A medical device, such as a catheter, having an alternative design distal tip, and method of using and making the same. In some embodiments, the distal tip includes a flared portion that extends away from the longitudinal axis of the medical device, and in some cases can be folded back so as to be atraumatic to tissues when advancing through a body orifice.

30 Claims, 4 Drawing Sheets

MEDICAL DEVICE WITH ATRAUMATIC TIP

FIELD OF THE INVENTION

The invention pertains to medical devices, and more particularly, to medical devices, such as catheters, having an alternative design distal tip.

BACKGROUND

A wide variety of catheters, for example intravascular catheters, such as diagnostic, therapeutic, and guide catheters, have been developed for medical interventions. These catheters generally include a catheter shaft that is advanced through the anatomy of a patient to a target region. Once properly situated, the catheter can be used for its intended purpose or as a guide for other interventions.

SUMMARY

The invention pertains to design, material, method of manufacturing, and method of use alternatives for medical devices. In some embodiments, the invention relates to a medical device, such as a catheter, having an alternative design for a distal tip disposed at a distal portion thereof.

DETAILED DESCRIPTION

The following description should be read with reference to the drawings wherein like reference numerals indicate like elements throughout the several views. The detailed description and drawings illustrate some example embodiments of the claimed invention.

Figures 1, 2, 4, 5:
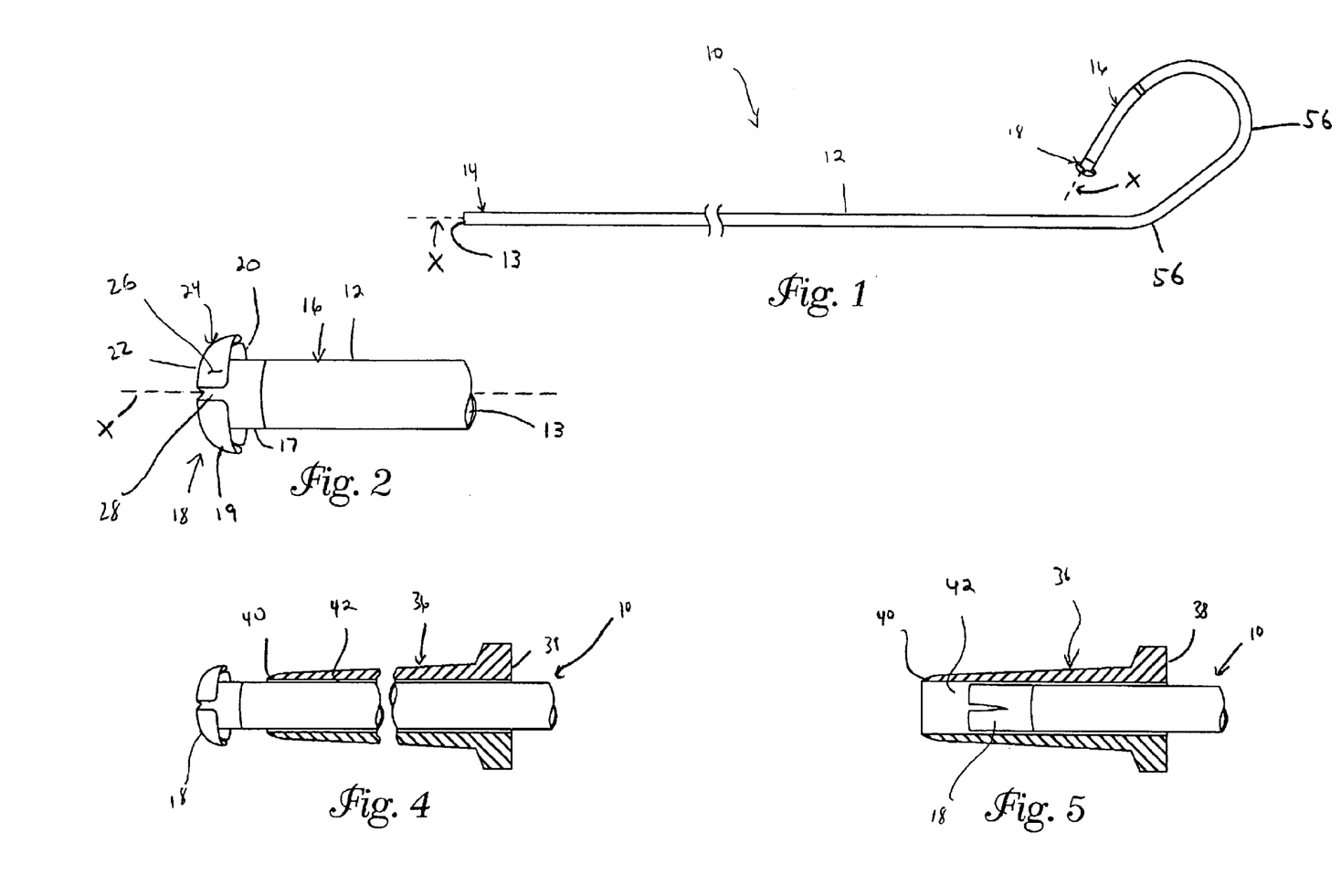
FIG. 1 is a plan overview of a catheter including a distal tip.
FIG. 2 is an enlarged view of the distal tip of the catheter of FIG. 1.
FIG. 4 is a partial cross-sectional view showing the catheter of FIG. 1 disposed within a loading tool.
FIG. 5 is a partial cross-sectional view of the catheter of FIG. 1 after back-loading the distal tip into the loading tool.

FIG. 1 is a plan overview of a catheter 10. The catheter 10 includes a generally elongated shaft 12 extending along a central or longitudinal axis x. The axis x extends along the length of the catheter 10 and necessarily follows the shape or curvature of the catheter shaft 12. The catheter shaft 12 has a proximal portion 14 and a distal portion 16. A distal tip 18 is disposed at the distal end of the distal portion 16. The distal tip 18 has a configuration that in some embodiments is designed to be atraumatic, and in some embodiments, is designed to allow other devices to be funneled or otherwise more easily pass into a lumen defined by shaft 12 through the distal tip 18. The specific structure of some embodiments of the distal tip 18 will be discussed in more detail below.

For purposes of illustration only, catheter 10 is depicted in FIG. 1 as an intravascular catheter, and in particular, an intravascular guide catheter. However, it can be appreciated that catheter 10 can be any one of multiple different intravascular or non-intravascular catheter types. A person of ordinary skill in the art will be familiar with different types of catheters appropriate for multiple embodiments. Some examples of other intravascular catheters include, but are not limited to, diagnostic catheters, balloon catheters, atherectomy catheters, stent delivery catheters, and the like. Moreover, although discussed with specific reference to catheters, the invention can be applicable to almost any medical device having an elongated shaft with multiple shaft sections with a distal tip. For example, the alternative distal tip construction is contemplated for use with medical devices such as guidewires, intravascular rotational devices, or the like.

Referring back to FIG. 1, the shaft 12 can be manufactured, include structure, and be made of materials so as to provide the desired characteristics of the catheter 10, depending upon the intended use. For example, the shaft 12 can be manufactured using structure and materials so as to maintain a desired level of flexibility and torquability appropriate for maneuvering the catheter 10 as desired, for example, through the vasculature of a patient. In some embodiments, the catheter 10 can include a shaft 12 that is generally characterized as having a tubular member construction that includes at least a single lumen 13 extending the length of shaft 12 along longitudinal axis x. The lumen 13 within the shaft 12 can possess an inner diameter capable of transmitting fluids, or in some cases, receiving another medical device, such as a guidewire or another catheter, for example, a diagnostic catheter, a balloon catheter, a stent delivery catheter, or the like. In some embodiments, the lumen within shaft 12 is adapted and configured to accommodate another medical device having outer diameters in the range of 1F–10F.

The shaft 12 can be manufactured from any suitable material to impart the desired characteristics. Examples of some suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa.

The shaft 12 can have a single-layer tubular construction or a multi-layer tubular construction. For example, in some particular embodiments, the shaft 12 can have a three layer tubular construction including an inner tubular layer, a reinforcing layer disposed about the inner tubular layer, and an outer tubular layer disposed about the reinforcing layer. In some such embodiments, the inner tubular layer can be made of a lubricious material, for example tetrafluoroethylene (PTFE), or a copolymer of tetrafluoroethylene with perfluoroalkyl vinyl ether (PFA) (more specifically, perfluoropropyl vinyl ether or perfluoromethyl vinyl ether), or the like.

The reinforcing layer can be constructed with any suitable materials and structures to impart the desired characteristics to the shaft. The reinforcing layer can include one or more support members that can comprise, for example, a braid, a coil, a filament or wire, or series of such structures, or the like. Examples of suitable materials for constructing the reinforcing layer include polymers, metals, or metal alloys such as stainless steel, nickel titanium alloys, tungsten, or the like.

The outer layer can be made up of one or more outer tubular segments disposed over the reinforcing layer, and can be constructed with any suitable materials and structures to impart the desired characteristics to the shaft. For example, the outer tube can comprise any of the shaft materials listed above, and in some embodiments can include nylon, polyether block amide (PEBA), or a blend of the two and in some embodiments can have a durometer on the order of about 5–90D. In some embodiments, a PEBA polymer is used to form the outer tubular member, and in some embodiments PEBAX® is used. The material of the outer layer can be blended with a liquid crystal polymer (LCP). For example, the mixture can contain up to about 5% LCP. This has been found to enhance torqueability. The outer tubular layer can be made up of a plurality of outer tubular segments made of materials having different durameters to impart varying degrees of flexibility to different sections of the shaft. The shaft can be constructed using any appropriate technique, for example, by extrusion, a heat bonding process, molding, and the like.

Some other examples of suitable catheter shaft constructions and materials can be found in U.S. Pat. Nos. 5,569,218; 5,603,705; 5,674,208; 5,680,873; 5,733,248; 5,853,400; 5,860,963; and 5,911,715, all of which are incorporated herein by reference.

The catheter 10 can be curved or shaped as desired. For example, catheters, such as guide catheters, can include a variety of shapes specific for different bodily passages and procedures. The stabilization of a catheter's position within a patient's anatomy is often achieved through curves or bends 56 imparted into shaft 12 by the manufacturer. These preformed curves 56 act by anchoring a selected portion of shaft 12 against an opposing wall within a patient's vasculature or other body portion. Proper anchoring is often achieved by matching the predisposed shape of the curved shaft 12 with the general curved anatomical shape around a targeted site. In vascular procedures involving treatment to one of the coronary arteries, often a curve is imparted proximate the distal portion 16 of shaft 12 with the intention of placing the catheter's distal tip 18 at a desired angle. In embodiments of catheter 10 that are designed for a procedure in a coronary artery, for example, shaft 12 can be shaped so that when it is inserted through the aorta of the patient, the curvature of shaft 12 will place distal tip 18 at an angle that engages one of the coronary ostia. Those of skill in the art recognize some different shapes by names such as Judkins Right, Judkins Left, Amplatz Right, Amplatz Left, Bentson, Shepherd Hook, Cobra, Headhunter, Sidewinder, Newton, Sones and others, each formed in a different shape.

Referring to FIG. 2, the distal tip 18 is connected to the shaft 12 and extends about the longitudinal axis x. The distal tip 12 further defines the lumen 13, and includes a proximal portion 17 and an end portion 19 that is flared such that the walls of the end portion 19 extend at an angle different from the longitudinal axis x. The end portion 19 can be flared such that it extends outwardly at an angle away from the longitudinal axis x. In the embodiment shown, the end portion 19 of tip 18 is flared outwardly and extends in a curved fashion in a direction away from the longitudinal axis x, and continues to extend around in a hook shaped fashion, and extends in a proximal direction relative to the longitudinal axis x. The tip 18 includes a distal end 20 and a distal terminus 22. When configured in the flared or folded position, as shown in FIG. 2, the distal terminus 22 is located distally of distal end 20 along the longitudinal axis x. It can be appreciated that the spatial distribution of distal terminus 22 and distal end 20 are generally measured with respect to the longitudinal axis x, regardless of the curvature of the shaft 12. Thus, the distal direction along the longitudinal axis x of shaft 12 is directed toward distal portion 16 and the proximal direction is directed toward proximal portion 14 along the longitudinal axis x. According to this embodiment, when tip 18 is in the folded or flared configuration, distal end 20 is disposed at a location that is in the proximal direction from distal terminus 22 along the longitudinal axis x. Additionally, the distal end 20 is disposed and terminates at a point that is further from the longitudinal axis than the proximal portion 17 of the distal tip 18.

Figure 8:
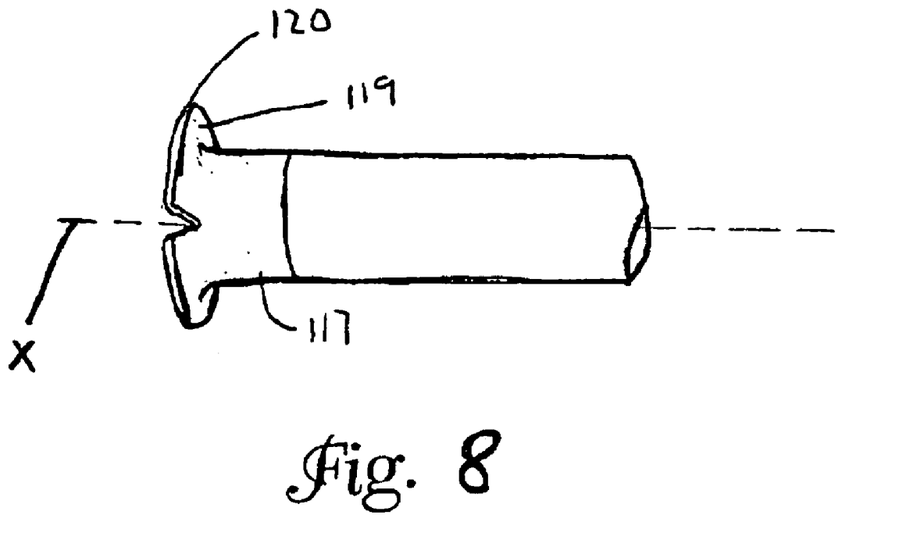
FIG. 8 is an enlarged view of a distal tip of a catheter in accordance with another example embodiment.

In other embodiments, the distal end can be flared away from the longitudinal axis x, but with less of a hook shape such that the distal end is not necessarily pointing in a proximal direction or disposed proximally of the distal terminus, along the longitudinal axis x. For example, an alternative tip construction is shown in FIG. 8. In this embodiment, the distal tip 118 includes a proximal portion 117 and an end portion 119 that is flared away from the longitudinal axis x, and extends in a curved manner, but does not turn in a proximal direction along the axis x. In this embodiment, the distal end 120 is pointed in an outward direction that is generally perpendicular to the longitudinal axis x.

In yet other embodiments, it is contemplated that the end portion can be flared outwardly at an angle away from the longitudinal axis, but the end portion would still extend distally. Thus, in such embodiments, the distal end would still be the distal terminus. It will also be understood that in other embodiments, the end portion can be flared such that it extends in a generally perpendicular or diagonal fashion at an angle away from the longitudinal axis x, and is not necessarily curved in shape.

Referring back to FIG. 2, in this embodiment, the distal tip 18 includes a mouth region 24 defined by the widest portion of tip 18. Mouth region 24 includes an inside diameter. The shaft 12 also has an inside diameter. The inside diameter of mouth region 24 is generally larger than the inside diameter of shaft 12. In some embodiments, this allows tip 18 to act similar to a funnel for directing objects into shaft 12 (i.e., the lumen 13 of shaft 12). The funneling feature can bestow several beneficial features to tip 18 and catheter 10. For example, this feature can make it easier to retract another medical device, for example a therapeutic catheter, into shaft 12 through the distal tip 18.

The shape of tip 18 or portions thereof can vary between different embodiments. For example, a fold region 26 can be defined between distal terminus 22 and distal end 20. Fold region 26 can include portions that bend toward, are substantially parallel with, or bend away from the outer surface of the shaft 12. Moreover, one or more slits 28 can be formed in tip 18, for example, within fold region 26. These and other alterations can be incorporated to enhance the desired characteristics of the distal tip 18.

The distal tip can have a single layer tubular construction or a multilayer tubular construction, depending upon the material used and the desired characteristics. Furthermore, the wall thickness of tip 18 can be generally constant, or can taper. For example, tip 18 can have a thicker wall proximate distal portion 16 that tapers as it extends toward the distal end 22. Alternatively, tip 18 can distally increase in thickness.

The distal tip 18 can be made of any suitable materials, for example polymers, metals, or metal alloys. Any of the materials listed above for use in the shaft portion are contemplated for use in the distal tip 18. In some embodiments, tip 18 is generally comprised of a flexible material so that tip 18 can be folded back. This embodiment would allow tip 18 to shift between a folded position as shown in FIG. 2 and a generally elongated position that can allow for easier insertion of tip 18 into a blood vessel or other body orifice (please see FIGS. 4 and 5, and the discussion pertaining thereto). Additionally, a soft or flexible distal tip can allow catheter 10 to navigate and traverse the tortuous pathways of a patient's vasculature, or mate with a target site within the vasculature, in a generally atraumatic manner. Alternatively, tip 18 can be comprised of a more rigid material, which can provide enhanced strength or resistance to deformation. The later embodiment can be useful in applications such as passing a chronic total occlusion or stenosis.

Some specific examples of suitable polymeric materials for distal tip 18 include, but are not limited to a polyethylene, polyamide, polyether-ester (for example, a polyether-ester available under the tradename HYTREL), or block copolymer such as polyether block amide (PEBA), for example that available under the trade name PEBAX®. In some embodiments, the material of the distal tip has a lower durometer than the shaft materials. In some embodiments, the tip material has a durameter in the range of about 30D to about 70D, and in some embodiments, in the range of about 70D to about 100D. In some alternative embodiments, the last portion of the tip at its distal end can be made of a different material from the tip material to form a tip extension. In some such embodiments, the last portion is made from a material that is more durable relative to the softer tip material. In particular, the more durable material will resist deforming or tearing when in use, such as in tracking the patient's tortuous anatomy. For example, this last portion can be manufactured from Marlex high-density polyethylene. This distal tip 18 material selection can improve the integrity of the tip region at its distal-most end.

The distal tip can be connected to the shaft 12 using any generally suitable technique or construction. In some embodiments, distal tip 18 can be heat welded or bonded to the distal portion 16 of shaft 12. The distal tip 18 can be preformed into the desired shape prior to connection to the shaft 12, or can be formed into the desired shape during or after connection to the shaft 12. The distal tip can be given the desired shape using any generally suitable technique or construction, depending upon the materials used to make the tip. In some embodiments, the tip is shaped through molding, thermoforming or thermal-reforming, and the like.

Figure 3:
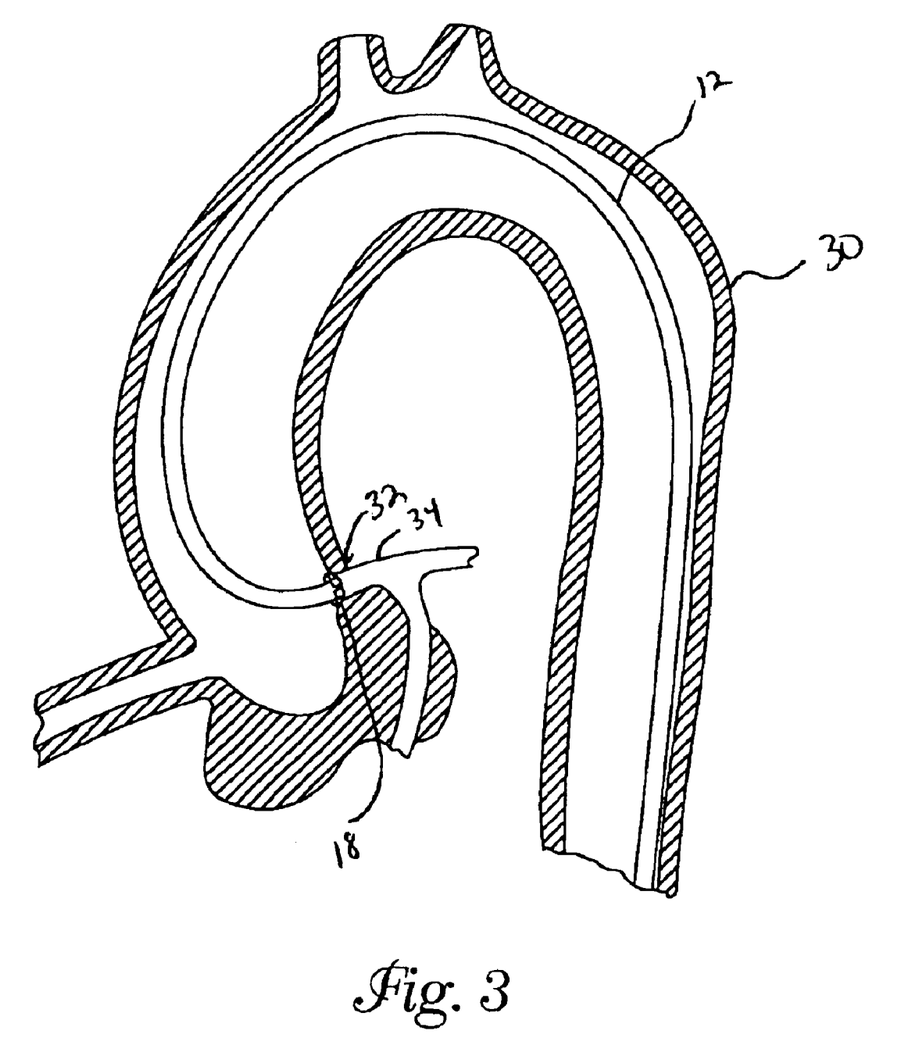
FIG. 3 is a perspective view of the catheter of FIG. 1 passing through an aorta of a patient and engaging an ostium of a coronary artery.

FIG. 3 is a plan view of catheter 10 passing through the aorta 30 or a patient and engaging the ostium 32 of the coronary artery 34. In this embodiment, distal tip 18 is of appropriate size and flexibility such that it will generally conform to the size of ostium 32. Tip 18 can be disposed at ostium 32 and substantially conform to the arterial walls. By conforming to the shape of the artery, tip 18 creates a target for a therapeutic catheter to aim at that is essentially the same size as the artery. Additionally, the distal tip 18 can aid in more atraumatic catheter navigation or atraumatic engagement of the distal tip with the ostium 32 within the patient's anatomy.

Also shown in FIG. 3, in some embodiments, if tip 18 substantially conforms to the arterial surface at ostium 32, slits 28 would allow for blood to pass into the coronary arteries 34. This allows catheter 10 to substantially conform to the artery without completely occluding blood flow. Additionally, in some embodiments, side holes can be formed in and around distal portion 16 to increase blood flow to the artery.

FIGS. 4 and 5 illustrate a method of shifting distal tip 18 between a folded configuration and an elongated configuration by using a loading tool 36. Shifting can be important in order to decrease the profile of tip 18 to make it easier to insert catheter 10 into a blood vessel or other anatomy. Loading tool 36 includes a proximal end 38, a distal end 40, and a central channel 42. The inside diameter of the channel 42 can be just large enough to accommodate catheter 10. By relatively tightly fitting over catheter 10, it becomes possible for distal tip 18 to be extended when disposed within channel 42.

To use tool 36, proximal region 14 of catheter 10 can be pre-loaded into tool 36 before proximal hub of catheter is attached (i.e., proximal region 14 can enter channel 42 at distal end 40, advanced through channel 42, and exit tool 36 at proximal end 38). Once disposed within channel 42, catheter can be further advanced until distal tip 18 approaches distal end 40 of tool 36. Further advancement of catheter 10 within channel 42 causes tip 18 to engage distal end 40, which forces tip 18 to begin to elongate or "unfold". The slits 28 can aid in allowing the tip 18 to transfer between the folded and unfolded positions. The elongated configuration (or partially elongated portion of tip 18) can then enter channel 42 as shown in FIG. 5.

Figure 6:
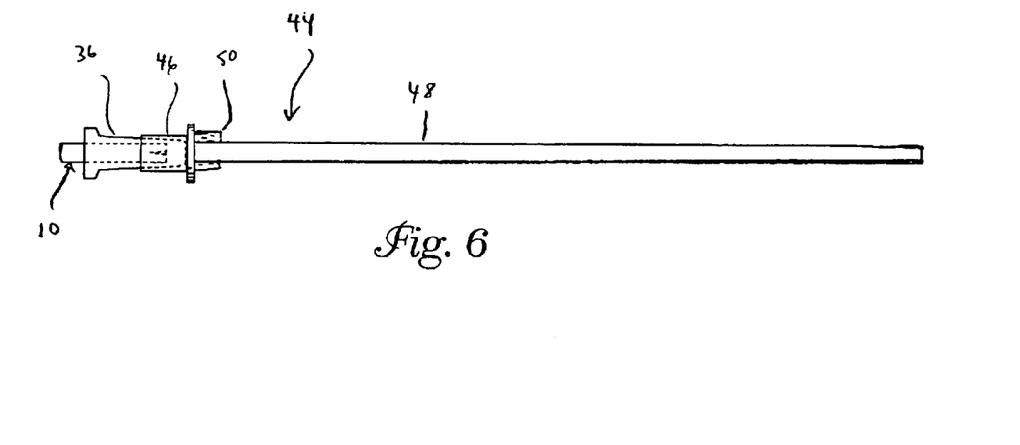
FIG. 6 is a perspective view of the catheter and loading tool of FIG. 5 being inserted into an insertion sheath.

Once in the elongated configuration, catheter 10 can then be introduced to the vasculature or other body orifice by use of, for example, an insertion sheath 44. One example of an insertion sheath 44 is illustrated in FIG. 6 and includes a proximal hub 46 adapted to receive tool 36 and an elongate distal tubular member 48 adapted to being inserted at least partially into a patient's anatomy, for example, into a blood vessel. Between hub 46 and distal tubular member 48 is a transition zone or strain relief 50. Transition zone 50 forms a smooth transition in diameter and stiffens between hub 46 and distal tubular member. It can be appreciated that the introducer sheath 44 is used to introduce the catheter 10 into the anatomy, for example the vasculature of a patient, as is generally known. For example, the elongate distal tubular member 48 can be inserted at least partially into a patient's anatomy, such as into an artery, for example the femoral artery. Once sheath 44 is properly placed, catheter tip 18 can be back-loaded into tool 36. Then, distal end 40 of tool 36 can be inserted into or otherwise coupled to hub 46. Catheter 10 can then be advanced through sheath 44 and into a patient's anatomy. Once the catheter is in the anatomy of the patient, the distal tip can shift from the first position back to the folded configuration.

Figure 7:
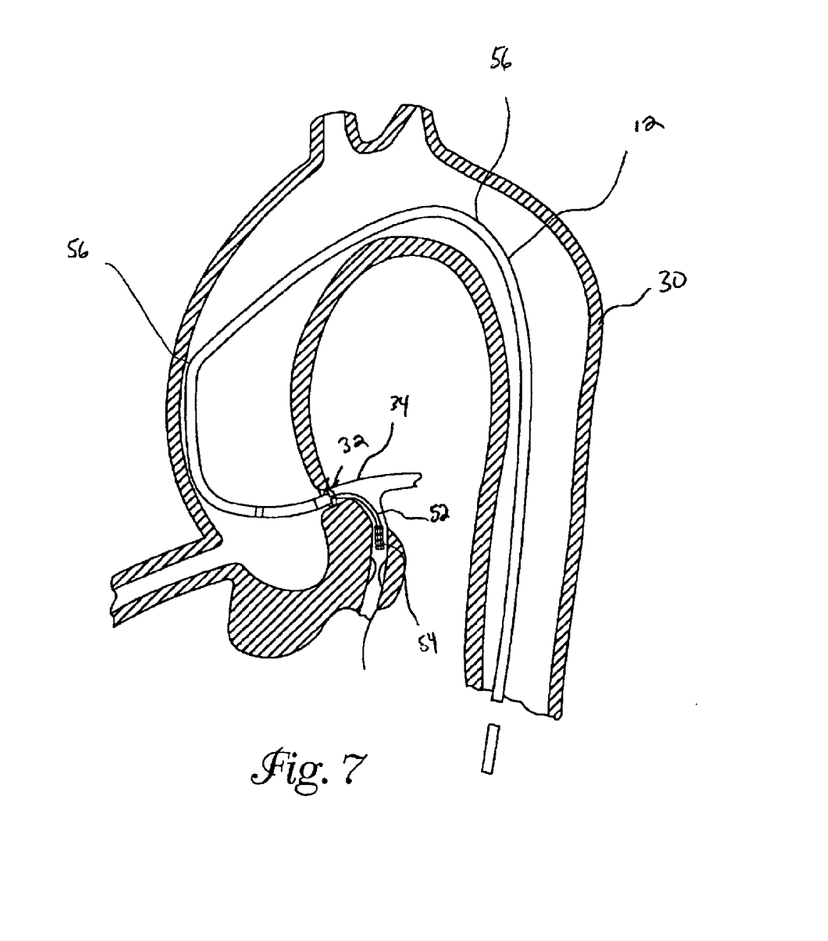
FIG. 7 is a partial cross-sectional plan view of the catheter of FIG. 1 being used in conjunction with a therapeutic catheter.

FIG. 7 is a partial cross-sectional plan view of catheter 10 being used in conjunction with a therapeutic catheter 52. In this example, therapeutic catheter 52 is a stent delivery catheter including a stent 54 attached thereto. During some procedures, it becomes necessary to remove the theraputic catheter, including the undeployed stent, from the vasculature of a patient, for example, after a failed attempt at stenosis. The stent, however, creates a widening in the outer diameter of the therapeutic catheter which could potentially "catch" on the distal tip of the guide catheter as it is being drawn back into the guide catheter. In this embodiment, however, the shape of the distal tip 18 on the guide catheter 10 acts as a funnel to facilitate the entry of the stent into the catheter 10. By funneling the stent into the guide catheter it would be less likely that the stent would "catch" on the guide catheter.

It should be understood that this disclosure is, in many respects, only illustrative. Changes can be made in details, particularly in matters of shape, size, and arrangement of steps without exceeding the scope of the invention. The invention's scope is, of course, defined in the language of the claims.

What is claimed is:

1. A medical device, comprising:
    an elongate shaft extending along a longitudinal axis, the shaft including a proximal portion, and a distal portion; and
    a distal tip disposed at the distal portion of the shaft, the distal tip including a proximal section disposed adjacent to the distal portion of the shaft, and a distal section, the distal section being pre-formed into a flared position wherein at least a part of the distal section extends at an angle away from the longitudinal axis such that the distal section includes a distal end that terminates at a point further from the longitudinal axis than the proximal section of the distal tip;
    wherein the distal tip is configured to be shifted through the application of a force by a loading tool from the flared position to a second position in which the distal section of the distal tip extends about the longitudinal axis such that the distal ten terminates at a point closer to the longitudinal axis than when in the flared position;
    wherein the distal tip is pre-formed such that it shifts from the second position back to the flared postion when the force is removed.

2. The medical device in claim 1, wherein the medical device comprises a guide catheter.

3. The medical device of claim 1, wherein when in the flared position, the distal section is folded back proximally so as to define a distal terminus, and the distal terminus is located distally of the distal end along the longitudinal axis.

4. The medical device of claim 3, wherein the shaft includes an exterior surface and when in the flared position the distal section includes a fold region between the distal terminus and the distal end, and at least a portion of the fold region extends parallel with the exterior surface of the shaft.

5. The medical device of claim 3, wherein the shaft includes an exterior surface and when in the flared position the distal section includes a fold region between the distal terminus and the distal end, and at least a portion of the fold region extends away from the exterior surface of the shaft.

6. The medical device of claim 3, wherein the shaft includes an exterior surface and when in the flared position the distal section includes a fold region between the distal terminus and the distal end, and at least a portion of the fold region extends toward the exterior surface of the shaft.

7. The medical device of claim 1, wherein the shaft defines a lumen having a diameter and wherein when in the flared position the distal section defines a mouth having a diameter that is greater than the diameter of the lumen.

8. The medical device of claim 1, wherein when in the flared position, the distal tip is configured to couple with an ostium.

9. A guide catheter, comprising:
    an elongate tubular guide catheter shaft extending along a longitudinal axis, the shaft defining only a single lumen, the lumen and shaft being sized and shaped to receive and guide a fluid or device within a body vessel to an opening defined within the body vessel, the shaft including a proximal portion, and a distal portion; and
    a distal tip disposed at the distal portion of the shaft, the distal tip including a flared portion that is folded back proximally so as to define a distal terminus and a distal end, wherein the distal terminus is located distally of the distal end along the longitudinal axis, and wherein the distal tip is sized and shaped to couple with the opening defined within the body vessel.

10. The guide catheter of claim 9, wherein the shaft includes an exterior surface and the distal tip includes a fold region between the distal terminus and the distal end, wherein at least a portion of the fold region extends parallel with the exterior surface of the shaft.

11. The guide catheter of claim 9, wherein the shaft includes an exterior surface and the distal tip includes a fold region between the distal terminus and the distal end, wherein at least a portion of the fold region bends away from the exterior surface of the shaft.

12. The guide catheter of claim 9, wherein the shaft includes an exterior surface and the distal tip includes a fold region between the distal terminus and the distal end, wherein at least a portion of the fold region bends toward the exterior surface of the shaft.

13. The guide catheter of claim 9, wherein the distal tip defines one or more slits formed therein.

14. The guide catheter of claim 9, wherein the lumen defines a diameter and wherein a mouth is defined at the distal terminus of the distal tip such that the mouth defines a diameter that is greater than the diameter of the lumen.

15. The guide catheter of claim 9, wherein the distal tip is sized and shaped to couple with an ostium.

16. A catheter for use in a body of a patient, the catheter comprising:
    an elongate shaft including a proximal portion, a distal portion, and a lumen extending therethrough; and
    a distal tip disposed at the distal portion, the distal tip including a distal terminus and a distal end, the distal tip being pre-formed into a first position wherein the distal tip is folded back proximally such that the distal terminus is located distally of the distal end;
    wherein the distal tip is configured to shifted through the application of a force using a loading means from the first position to a second position in which the distal end is located distally of the distal terminus and
    wherein the distal tip is pre-formed such that it shifts from the second position back to the first position when the force is removed.

17. The catheter of claim 16, wherein the distal tip includes a fold region between the distal terminus and the distal end when configured in the first position.

18. The catheter of claim 16, wherein the shaft includes one or more curves.

19. The catheter of claim 16, wherein the distal tip includes one or more slits.

20. The catheter of claim 16, wherein the distal tip includes one or more side holes therein.

21. The catheter of claim 16, wherein the shaft defines a lumen that has a diameter and a mouth is defined at the distal terminus of the distal tip when the distal tip is oriented in the first position, and wherein the mouth has a diameter that is greater than the diameter of the lumen.

22. The catheter of claim 16, wherein the distal tip when in the first position is configured to couple with an opening defined within a body vessel.

23. A method of advancing a catheter, the method comprising:
    providing a catheter including an elongate shaft having a distal tip, the distal tip including a distal end and a distal terminus, the distal tip being formed into a first position wherein the distal tip is folded back proximally such that the distal terminus is located distally of the distal end, wherein the distal tip is configured to be shifted from the first position and a second position in which the distal end is located distally of the distal terminus;

providing a loading tool having a lumen adapted for slidably receiving the catheter;

disposing the catheter into the lumen of the loading tool such that the distal tip engages the loading tool and shifts from the first position to the second position; and advancing the catheter into a blood vessel through an introducer sheath such that when the distal tip enters the blood vessel, the distal tip shifts from the second position back to the first position within the blood vessel.

24. A guide catheter, comprising:

an elongate tubular guide catheter shaft extending along a longitudinal axis, the guide catheter shaft defining only a single lumen, the lumen and shaft being sized and shaped to receive and guide a fluid or device within a body vessel to an opening defined within the body vessel, the shaft including a proximal portion, a distal portion, and a distal tip disposed at the distal portion, the distal tip including a proximal portion attached to the distal portion of the shaft, and a flared portion, wherein at least a portion of the flared portion extends perpendicularly from the longitudinal axis of the shaft, wherein the distal tip is sized and shaped to couple with the opening defined within the body vessel.

25. The catheter of claim 24, wherein the distal tip is sized and shaped to couple with an ostium.

26. A method of advancing a catheter comprising:

providing a catheter including an elongated shaft extending along a longitudinal axis, the shaft having a distal tip, the distal tip including a proximal portion disposed adjacent the shaft and a distal portion, the distal tip being formed into a first position wherein the distal portion of the distal tip extends at an angle away from the longitudinal axis, wherein the distal tip is configured to be shifted from the first position to a second position in which the distal portion of the distal tip extends about the longitudinal axis;

providing a loading tool having a lumen adapted for slidably receiving the catheter;

disposing the catheter into the lumen of the loading tool such that the distal tip engages the loading tool and shifts from the first position to the second position; and advancing the catheter into a blood vessel through and introducer sheath such that when the distal tip enters the blood vessel, the distal tip shifts from the second position back to the first position within the blood vessel.

27. A guide catheter, comprising:

an elongate tubular guide catheter shaft extending along a longitudinal axis, the shaft having a multi-layer tubular construction including an inner tubular layer defining a lumen configured to receive and guide a fluid or device within a body vessel to an opening defined within the body vessel, a reinforcing layer disposed about the inner tubular layer, and an outer tubular layer disposed about the reinforcing layer, the shaft including a proximal portion and a distal portion; and a distal tip disposed at the distal portion of the shaft, the distal tip being pre-formed into a first shape including a proximal portion disposed adjacent to the distal portion of the shaft, and a flared portion extending at an angle away from the longitudinal axis, the flared portion including a distal end that terminates at a point further from the longitudinal axis than the proximal portion of the distal tip, wherein the distal tip comprises flexible material such that when a force is applied to the distal tip with a loading tool, the distal tip is configured to shift from the first pre-formed shape to a second shape in which the distal portion of the distal tip extends about the longitudinal axis such that the distal end terminates at a point closer to the longitudinal axis than when in the first shape, and when the loading tool is removed from the distal tip, the distal tip, due to its pre-formed shape shifts from the second shape back to the first shape.

28. A guide catheter, comprising:

an elongate tubular guide catheter shaft extending along a longitudinal axis, the shaft having a multi-layer tubular construction including an inner tubular layer defining a lumen adapted to receive a guide a fluid or device within a body vessel to an opening defined within the body vessel, a reinforcing layer disposed about the inner tubular layer, and an outer tubular layer disposed about the reinforcing layer, the shaft including a proximal portion and a distal portion; and a distal tip disposed at the distal portion of the shaft, the distal tip being configured into a first pre-formed shape including a flared portion that is folded back proximally so as to define a distal terminus and a distal end, wherein the distal terminus is located distally of the distal end along the longitudinal axis, and wherein the distal tip is configured to couple with the opening defined within the body vessel, wherein the distal tip comprises flexible material such that when a force is applied to the distal tip by a shifting means, the distal tip is configured to shift from the first pre-formed shape to a second shape in which the distal end is located distally of the distal terminus, and when the shifting means is released from the distal tip, the distal tip shifts from the second shape back to the first pre-formed shape.

29. A guide catheter, comprising:

an elongate tubular guide catheter shaft extending along a longitudinal axis, the shaft defining a guidewire lumen, the guidewire lumen and shaft being sized and shaped to receive and guide a fluid or device with a body vessel to an opening defined within the body vessel, the shaft including a proximal portion, and a distal portion; and a distal tip disposed at the distal portion of the shaft, the distal tip including a flared portion that is folded back proximally so as to define a distal terminus and a distal end, wherein the distal terminus is located distally of the distal end along the longitudinal axis, and wherein the distal tip is sized and shaped to couple with the opening defined within the body vessel.

30. A guide catheter, comprising:

an elongate tubular guide catheter shaft extending along a longitudinal axis, the shaft defining a guidewire lumen, the shaft including a proximal portion, and a distal portion; and a distal tip disposed at the distal portion of the shaft, the distal tip including a flared portion that is folded back proximally so as to define a distal terminus and a distal end, wherein the distal terminus is located distally of the distal end along the longitudinal axis, and wherein the distal tip is sized and shaped to couple with the opening defined within the body vessel.

* * * * *

UNITED STATES PATENT AND TRADEMARK OFFICE
CERTIFICATE OF CORRECTION

PATENT NO. : 6,866,655 B2
DATED : March 15, 2005
INVENTOR(S) : Steven S. Hackett It is certified that error appears in the above-identified patent and that said Letters Patent is hereby corrected as shown below:

<u>Column 10,</u>
Line 3, after "...portion of the distal tip," and before "wherein the distal tip comprises...", and insert -- wherein the distal tip is configured to couple with the opening defined within the body vessel, --.

Signed and Sealed this

Seventh Day of June, 2005

JON W. DUDAS
*Director of the United States Patent and Trademark Office*